United States Patent [19]

Williams

[11] Patent Number: Plant 6,596

[45] Date of Patent: Feb. 7, 1989

[54] ROSE PLANT

[76] Inventor: J. Benjamin Williams, 2800 Elnora St., Silver Spring, Md. 20902

[21] Appl. No.: 75,000

[22] Filed: Jul. 17, 1987

[51] Int. Cl.[4] ..... A01H 5/00
[52] U.S. Cl. ..... Plt./4
[58] Field of Search ..... Plt./4

*Primary Examiner*—Robert E. Bagwill

[57] ABSTRACT

A new and distinct variety of rose plant of the climbing rose class, which was originated by my crossing Tropicana Climber as seed parent and Swarthmore as pollen parent; characterized by bright orange-red hybrid tea blooms with dark velvet overtones on the inner petals of the open flower, produced on a vigorous-growing, disease resistant climbing shrub with everblooming habit and outstanding winter hardiness.

1 Drawing Sheet

The present invention relates to a new and distinct variety of rose plant of the climbing shrub class, which was originated by my crossing the rose variety known as "Climbing Tropicana" (U.S. Plant Pat. No. 2,701) with the rose variety known as "Swarthmore" (U.S. Plant Pat. No. 2,444).

The new variety resulted from an extensive breeding program conducted by me and having for its objective to produce improved, everblooming, orange and orange-red blended flowering shrub type climbing rose varieties, and it is one which fully achieves this objective, as evidenced by the following unique combination of characteristics which are outstanding therein and which distinguish the new variety from its parents, as well as from all other varieties of which I am aware:

1. An everblooming, bushy, free-standing, vigorous, upright-spreading, climbing habit which can be left as a large, bushy shrub, or trained as a typical climbing plant having long arching or climbing canes up to six to eight feet in length on first year plants. This new variety is distinctive from both its parents in that it produces blooming lateral canes all along the new main arched canes as they are produced.

2. The plant is ever-blooming and produces large 4 inch to 4½ inch flowers that last well and are produced singly and in clusters of three to five blooms to a spray.

3. Delicate old rose fragrance.

4. The general tonality of the flowers corresponds to deep orange red with a light overcast of dark velvet orange red on the inner surface of each petal. The flowers are long-lasting, finishing to a delicate orange red and coral pink blend.

5. The strong-growing plant has good hardiness and disease resistance.

Asexual reproduction of the new variety by budding, as performed at West Grove, Pa., U.S.A., and McFarland, Calif., U.S.A., shows that the aforementioned characteristics and distinctions come true to form and are established and transmitted through succeeding propagation.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (RHSCC) except where general color terms of ordinary dictionary significance are observed. The terminology used in color description herein refers to plate numbers in the aforementioned color chart, e.g., "41-C" is plate 41-C of The Royal Horticultural Society Colour Chart.

Parentage: Seedling.
*Seed parent.*—"Tropicana Climber".
*Pollen parent.*—"Swarthmore".
Class: Climbing shrub.

The following observations are made of specimens grown outdoors at West Grove, Pa., during the month of September.

FLOWER

Blooming habit: Recurring, continuous.

A. Bud:
- (1) *Size.*—Large.
- (2) *Form.*—High-centered, exhibition.
- (3) *Color.*—When sepals first divide: near 42-A. When petals begin to unfurl, color is near 42-A on edge of inner petal with a blending downward to the base of attachment varying in color from 42-B to 42-C.
- (4) *Sepals.*—Short and pointed.
- (5) *Peduncle.*—Length 3½ to 4 inches. Aspect — smooth. Strength — erect and heavy. Color.—137-D.

B. Bloom:
- (1) *Size.*—Large, average size when fully expanded is 4–4½".
- (2) *Borne.*—Singly on long canes, and several together on short branching canes.
- (3) *Form.*—High centered with good recurl.
- (4) *Petalage.*—40.
- (5) *Color.*—During first two days. Center of flower — a blending of 42-B and 42-C. Outer petals are near 40-A with an overlay of 42-B. Base of petals: 41-C. Reverse of petals — 44- C.
- (6) *Color change.*—General tonality from a distance — near 40-A, with a blending of 42-B and 42-C. Undertones of 41-C give a soft coral cast to the flowers as they finish. Color is attractive and uniform and highlights the contrasting foliage well until the petals drop.

C. Petals:
- (1) *Texture.*—Thick with good substance.
- (2) *Appearance.*—Inside velvety; outside satiny.

(3) *Form.*—Ovoid to pointed at tip.
(4) *Arrangement.*—Symetrically arranged in a circular outline.
(5) *Petaloids in center.*—Few.
(6) *Persistence.*—Drops off cleanly.
(7) *Fragrance.*—Delicate old rose.
(8) *Lasting quality.*—Good on plant, and as cut flower.

REPRODUCTIVE ORGANS

A. Stamens, anthers: Medium sized, many arranged around styles.
(1) *Color.*—Yellow-orange, near to 14-C.
B. Pollen: Color is yellow-orange, near to 21-D.
C. Styles: Uniform, even length.
D. Stigmas:
*Color.*—Yellow-orange — 17-C.
E. Hips: Large, rounded, near 28-B when ripe.

PLANT

A. Form: Climber.
B. Growth: Vigorous, upright and free-standing (may be grown on trellis or support).
*Height attained.*—Six to eight feet.
C. Foliage: Compound of 5 to 7 leaflets.
(1) *Size.*—Large.
(2) *Quantity.*—Abundant.
(3) *Color.*—New foliage: upper side — 137-A with leathery glossy foliage; under side — dull, near 147-C. Old foliage: upper side — 135-A, under side — 147-B.
(4) *Shape.*—Pointed.
(5) *Texture.*—Upper side — leathery with glossy finish. Under side — rough.

(6) *Edge.*—Serrated.
(7) *Serration.*—Small, primarily on tip.
(8) *Leaf stem.*—Color — 139-B; under side — 139-C.
(9) *Stipules.*—Medium length; slightly bearded.
D. Wood:
(1) *New wood.*—Color — 138-C. Bark — smooth.
(2) *Old wood.*—Color — 139-B. Bark — smooth.
E. Thorns:
(1) *Thorns.*—Quantity: on main stalks from base — ordinary; on laterals from stalk — few. Form: flat base, slightly hooked downward. Length: medium. Color when young — 47-C. Position: irregular.
(2) *Prickles.*—Quantity: On main stalks — none; on laterals — none.
F. Plant's disease resistance:
(1) *Mildew.*—Very good.
(2) *Blackspot.*—Very good.
(3) *Rust.*—None observed.
G. Winter hardiness: Excellent.

I claim:

1. A new and distinct variety of rose plant of the climber class, substantially as herein shown and described, characterized particularly as to novelty by its vigorous habit of growth, its good hardiness, its abundant and attractive foliage, its very good remontance, its habit of producing excellent formed blooms singly on long-stemmed canes and in clusters, the strong and appealing fragrance of its blooms, and the general color tonality of the flowers is bright orange-red, with dark velvet overtones on the inner petals of the open flower.

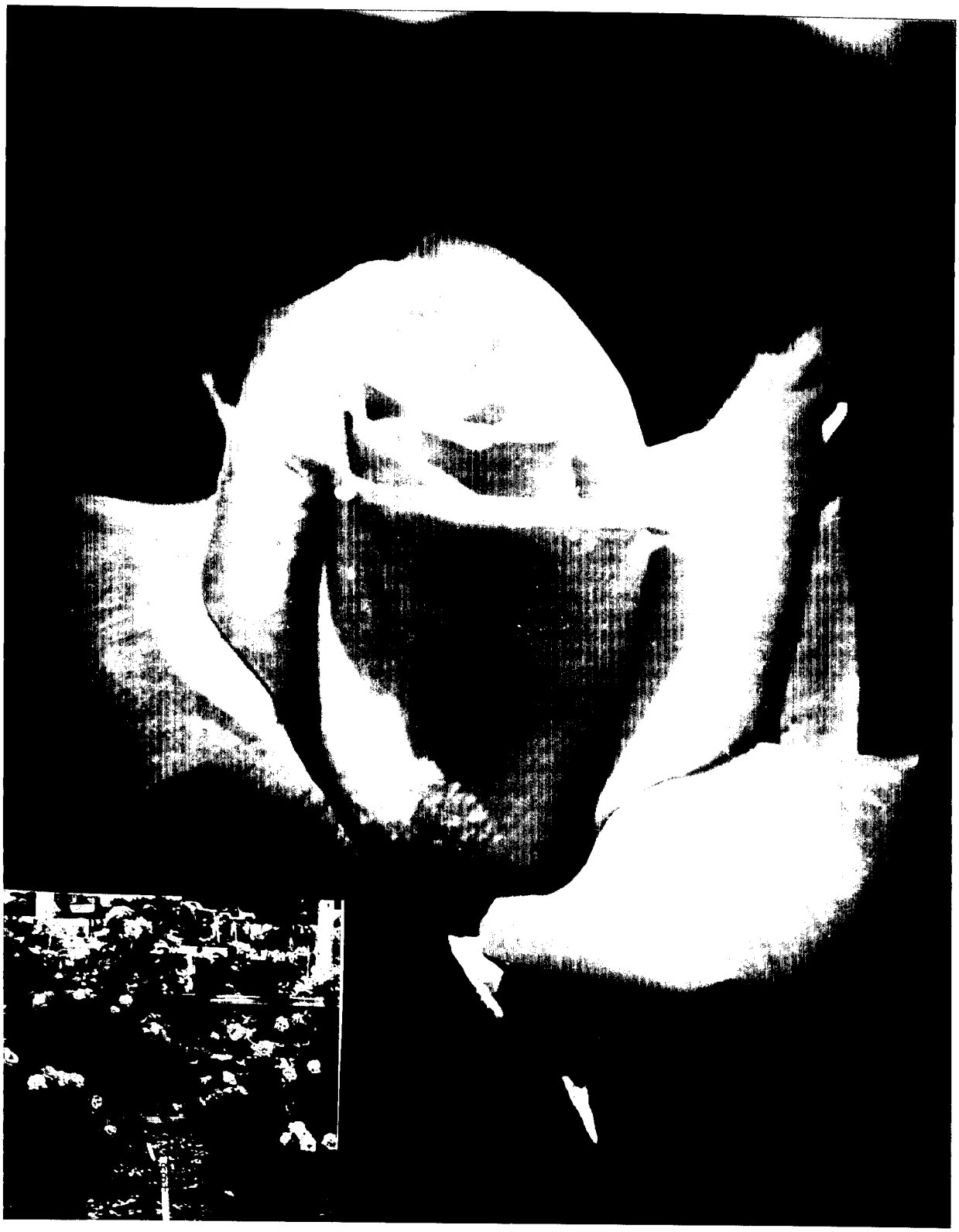

* * * * *